(12) United States Patent
Griengl et al.

(10) Patent No.: US 7,390,647 B2
(45) Date of Patent: Jun. 24, 2008

(54) METHOD FOR PRODUCING CHIRAL α-HYDROXYCARBOXYLIC CRYSTALLINE ACIDS

(75) Inventors: Herfried Griengl, Graz (AT); Ingrid Osprian, Graz (AT); Hans Schoemaker, AJ Geleen (NL); Christoph Reisinger, Graz (AT); Helmut Schwab, Graz (AT)

(73) Assignee: DSM Fine Chemicals Austria NFG GmbH & Co KG, Linz (AT)

( * ) Notice: Subject to any disclaimer, the term of this patent is extended or adjusted under 35 U.S.C. 154(b) by 351 days.

(21) Appl. No.: 10/544,103

(22) PCT Filed: Jan. 30, 2004

(86) PCT No.: PCT/EP2004/000859

§ 371 (c)(1),
(2), (4) Date: Aug. 2, 2005

(87) PCT Pub. No.: WO2004/076385

PCT Pub. Date: Sep. 10, 2004

(65) Prior Publication Data

US 2006/0099696 A1  May 11, 2006

(30) Foreign Application Priority Data

Feb. 27, 2003 (AT) ............................. A 285/2003

(51) Int. Cl.
*C12P 41/00* (2006.01)
(52) U.S. Cl. .................. 435/280; 435/146; 435/183; 435/252.1
(58) Field of Classification Search .................. 435/280, 435/146, 183, 252.1

See application file for complete search history.

(56) References Cited

U.S. PATENT DOCUMENTS

| | | | |
|---|---|---|---|
| 4,705,752 A | 11/1987 | Boesten et al. | |
| 5,580,765 A | 12/1996 | Hashimoto et al. | |
| 5,593,871 A * | 1/1997 | Anton et al. ................ | 435/129 |
| 5,736,385 A | 4/1998 | Tamura | |
| 5,756,306 A | 5/1998 | Yamaguchi et al. | |
| 6,133,421 A * | 10/2000 | Fallon et al. ................ | 530/350 |
| 6,869,783 B1 | 3/2005 | Ress-Löschke et al. | |
| 2006/0099696 A1 | 5/2006 | Griengl et al. | |
| 2006/0199256 A1 | 9/2006 | Griengl et al. | |
| 2007/0196905 A1* | 8/2007 | Burns et al. ................ | 435/128 |

FOREIGN PATENT DOCUMENTS

| | | |
|---|---|---|
| DE | 198 48 129 | 4/2000 |
| EP | 0 610 048 | 8/1994 |
| EP | 0 711 836 | 5/1996 |
| EP | 0 773 297 | 5/1997 |

OTHER PUBLICATIONS

International Search Report for PCT/EP2004/000859 completed May 4, 2004, three pages.
Mei-Xiang Wang et al; "Enantioselective biotransformations of racemic a-substituted α-substituted phenylacetonitriles and phenylacetamides using *Rhodococcus* sp. AJ270"; Tetrahedron: Asymmetry 11 (2000) 1123-35.
Ingrid Osprian et al; "Biocatalytic hydrolysis of cyanhydrins: an efficient approach to enantiopure α-hydroxy carboxylic acids"; Journal of Molecular Catalysis B: Enzymatic 24-25 (2003) 89-98; XP-002278959.

* cited by examiner

*Primary Examiner*—Herbert J. Lilling
(74) *Attorney, Agent, or Firm*—Nixon & Vanderhye P.C.

(57) ABSTRACT

The invention relates to a method for producing chiral α-hydroxycarboxylic crystalline acids consisting in transforming cyanhydrins (R) or (S) into α-hydroxycarboxylic acids (R) or (S), respectively by enzymatic hydrolysis in the presence of *Rhodococcus erythropolis* NCIMB 11540.

10 Claims, 1 Drawing Sheet

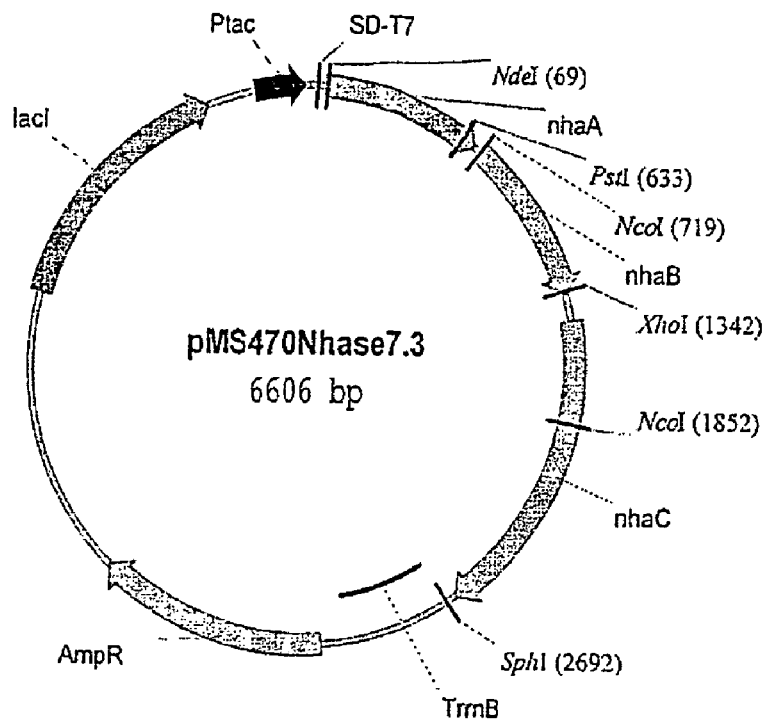
Figure 1: Plasmid map of pMS470Nhase7.3
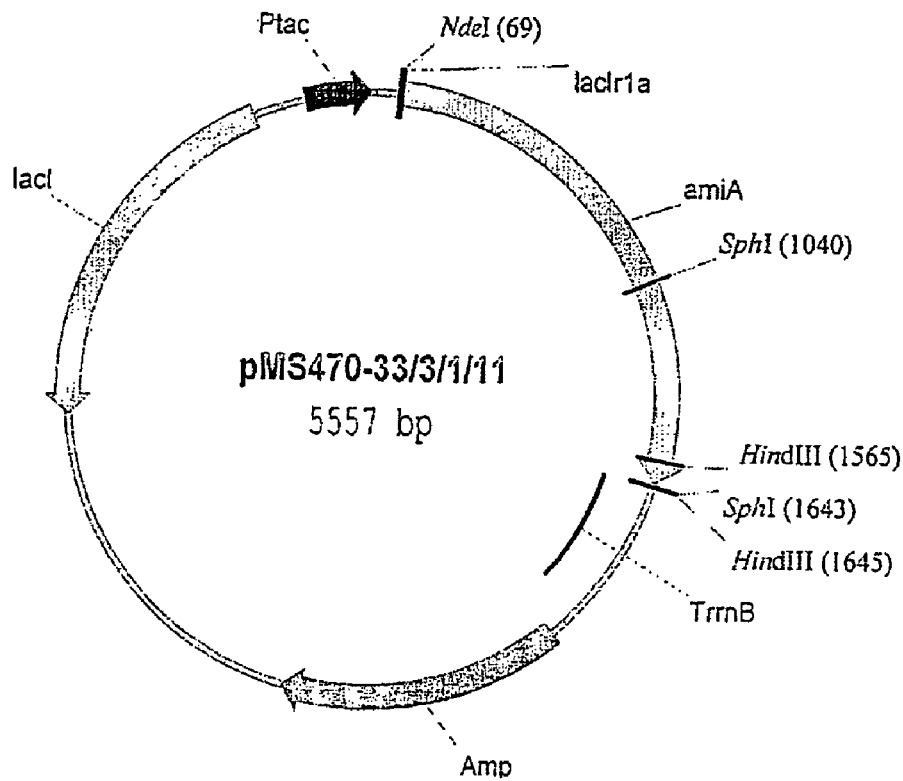
Figure 2: Plasmid map of pMS470-33/3/1/11

METHOD FOR PRODUCING CHIRAL α-HYDROXYCARBOXYLIC CRYSTALLINE ACIDS

This application is the US national phase of international application PCT/EP2004/000859 filed 30 Jan. 2004 which designated the U.S. and claims benefit of AT A 285/2003, dated 27 Feb. 2003, the entire content of which is hereby incorporated by reference.

BACKGROUND OF THE INVENTION

Optically active α-hydroxycarboxylic acids are used, for example, as additives to feeds, or in the production of pharmaceutical active compounds, vitamins and liquid crystals.

These optically active α-hydroxycarboxylic acids may, in addition, be advantageously converted, for example according to Effenberger et al., Angew. Chem. 95 (1983) No. 1, page 50, into N-substituted optically active α-amino acids which are otherwise prepared only with great difficulty.

Chiral α-hydroxycarboxylic acids are nowadays accessible chemically, by fermentation, or enzymatically.

The literature accordingly discloses a number of various methods for synthesis of chiral α-hydroxy-carboxylic acids.

For instance, racemic cyanohydrins, with addition of suitable microorganisms, can be hydrolyzed to give the desired chiral α-hydroxycarboxylic acids.

Production of chiral α-hydroxycarboxylic acids, especially the production of optically active lactic acid or mandelic acid, from racemic cyanohydrins using various microorganisms of the genera *Alicaligenes, Pseudomonas, Acinetobacter, Rhodococcus, Candida* etc. is described, for example, in EP 0 449 684, EP 0 527 553, EP 0 610 048, etc.

From this prior art, it is also known that when a racemic cyanohydrin is enzymatically hydrolyzed to the conjugate α-hydroxycarboxylic acid in the presence of a nitrilase, the problem occurs that the enzyme is inactivated within a short time and thus the desired α-hydroxycarboxylic acid is usually abtained only in low yields and concentrations. This also applies to the use of nitrile hydratases, which convert the cyanohydrin to the conjugate α-hydroxyamide. The hydroxyamides can then in turn be converted to the conjugate α-hydroxycarboxylic acids.

It is also known, for example from Angew. Chem. 1994, 106, page 1615f., that optically active cyanohydrins may be hydrolyzed by concentrated hydrochloric acid, without racemization, to give the conjugate chiral α-hydroxycarboxylic acids. The optical purity of the chiral α-hydroxycarboxylic acids thus produced corresponds here to the optical purity of the chiral cyanohydrin used, even if this is obtained in situ by enzyme-catalyzed addition of a cyanide group to a conjugate aldehyde or a ketone and is further processed without isolation or purification.

It is disadvantageous with this reaction that sensitive substrates are decomposed, and the occurrence of corrosion.

SUMMARY OF THE INVENTION

It was an object of the present invention to find a method in which nitriles as polar as chiral cyanohydrins can be converted using a mild and efficient method into the conjugate chiral hydroxycarboxylic acids, the hydroxycarboxylic acids having about the same enantiomeric purity as the cyanohydrins.

Unexpectedly, this object has been achieved by the use of a special bacterium from the genus *Rhodococcus*.

BRIEF DESCRIPTION OF THE DRAWINGS

FIG. 1 illustrates the map of the plasmid pMS470Nhase7.3 (6606 bp).

FIG. 2 illustrates the map of the plasmid pMS470-33/3/1/11 (5557 bp).

DETAILED DESCRIPTION OF THE INVENTION

The present invention therefore relates to a method for producing chiral α-hydroxycarboxylic acids, which comprises converting (R)- or (S)-cyanohydrins by enzymatic hydrolysis in the presence of *Rhodococcus erythropolis* NCIMB 11540 into the conjugate (R)- or (S)-α-hydroxycarboxylic acids.

In the inventive method, (R)- and (S)-cyanohydrins are converted into (R)- and (S)-α-hydroxycarboxylic acids with an optical purity of up to >99% ee.

(R)- and (S)-cyanohydrins which are produced by enzymatic or chemically catalyzed addition of a cyanide group to the corresponding aldehydes or ketones serve as starting compounds.

The enzymatic or chemically catalyzed addition of a cyanide group to the corresponding aldehydes or ketones can be performed here in a similar manner to the prior art, for example in a similar manner to EP 0 951 561, EP 0 927 766, EP 0 632 130, EP 0 547 655, EP 0 326 063, etc.

Suitable starting compounds are the aldehydes and ketones cited in the prior art.

Examples of suitable aldehydes are aliphatic, aromatic or heteroaromatic aldehydes. Aliphatic aldehydes are taken to mean saturated or unsaturated aliphatic, straight-chain, branched or cyclic aldehydes. Preferred aliphatic aldehydes are straight-chain aldehydes having in particular 2 to 18 carbon atoms, particularly preferably 2 to 12, which are saturated or monounsaturated or polyunsaturated. The aldehyde can have not only C—C double bonds, but also C—C triple bonds. The aldehyde can be unsubstituted or monosubstituted or polysubstituted by groups inert under the reaction conditions, for example by optionally substituted aryl or heteroaryl groups, such as phenyl or indolyl groups, by $C_1$-$C_6$-alkyl, optionally substituted cycloalkyl groups, which can have one or more heteroatoms from the group O, S, P or N, halogen, ether, alcohol, acyl, carboxylic acid, carboxylic ester, nitro or azido groups.

Examples of aromatic or heteroaromatic aldehydes are benzaldehyde or variously substituted benzaldehydes, for instance 2-chlorobenzaldehyde, 3,4-diflurobenzaldehyde, 4-methylbenzaldehyde, 3-phenoxy-benzaldehyde, 4-fluoro-3-phenoxybenzaldehyde, in addition furfural, anthracene-9-carbaldehyde, furan-3-carbaldehyde, indole-3-carbaldehyde, napththalene-1-carbaldehyde, phthaldialdehyde, pyrazole-3-carbaldehyde, pyrrole-2-carbaldehyde, thiophene-2-carbaldehyde, isophthalaldehyde or pyridinealdehydes, etc.

Examples of ketones are aliphatic, aromatic or heteroaromatic ketones in which the carbonyl carbon atom is unevenly substituted. Aliphatic ketones are taken to mean straight-chain, branched or cyclic ketones. The ketones can be saturated or monounsaturated or polyunsaturated. They can be unsubstituted or monosubstituted or polysubstituted by groups inert under the reaction conditions, for example by optionally substituted aryl or heteroaryl groups such as phenyl or indolyl groups, by halogen, ether, alcohol, acyl, carboxylic acid, carboxylic ester, nitro or azido groups.

Examples of aromatic or heteroaromatic ketones are acetophenone, indolyl acetone, etc.

Preference is given to (R)- or (S)-cyanohydrins of the formula

(I)

where R1 and R2 independently of one another are H, a $C_1$-$C_6$-alkyl or $C_1$-$C_6$-alkenyl radical which is optionally monosubstituted or polysubstituted by substituents inert under the reaction conditions, or a phenyl radical which is optionally monosubstituted or polysubstituted by substituents inert under the reaction conditions, with the proviso that R1 and R2 are not both H.

Preferred substituents inert under the reaction conditions are, for example, halogens, such as fluorine, bromine and chlorine, $C_1$-$C_6$-alkyl or $C_1$-$C_6$-alkoxy, ether, ester, acetals or optionally substituted phenyl and phenyloxy.

Particularly preferably, suitable compounds for the inventive method are (R)- or (S)-cyanohydrins, for instance (R)- or (S)-2-hydroxy-4-phenylbutyronitrile, (R)- or (S)-2-chloromandelonitrile, (R)- or (S)-mandelonitrile, (R)- or (S)-4-methylmandelonitrile, (R)- or (S)-3-phenoxymandelonitrile, (R)- or (S)-2-hydroxy-2-methylheptanenitrile, (R)- or (S)-2-hydroxy-2-phenylpropionitrile, (R)- or (S)-2-hydroxy-3-pentenenitrile, (R)- or (S)-1-hydroxycyclohexanenitrile, (R)- or (S)-acetophenonecyanohydrin.

The corresponding (R)- or (S)-cyanohydrin is then enzymatically hydrolyzed according to the invention.

The enzymatic hydrolysis is performed according to the invention in the presence of Rhodococcus erythropolis NCIMB 11540.

With Rhodococcus erythropolis NCIMB 11540, unexpectedly, a microorganism has been found which is distinguished in that it has a nitrile hydratase/amidase enzyme system available which can hydrolyze the nitrile function of nitrites which are polar in such a manner as the above-listed cyanohydrins.

By means of the nitrile hydratase/amidase enzyme system of Rhodococcus erythropolis NCIMB 11540, the chiral cyanohydrins are hydrolyzed in the first step by the nitrile hydratase into the conjugate chiral hydroxyamide which is then converted in a second hydrolysis step by the amidase into the corresponding chiral α-hydroxycarboxylic acid.

The microorganism can be used in the inventive method in any desired form, for example in the form of ground cells, crude or purified enzymes, recombinant enzymes, immobilized cells or enzymes, lyophilized cells, or "resting cells".

Preferably, use is made of recombinant enzymes, resting cells or lyophilized cells, particularly preferably recombinant enzymes or resting cells.

In addition to the direct use of nitrile hydratase/amidase-active preparations of Rhodococcus erythropolis NCIMB 11540 cells, the use of recombinant preparations expressed in a suitable microorganism, for instance E. coli, Pichia pastoris, Saccharomyces, Asperagillus, K. Lactis, etc. is a good alternative. The corresponding genes are introduced using plasmid constructs into suitable host cells, for example into E. Coli, Pichia pastoris, Saccharomyces, Asperagillus, K. Lactis host cells. By choosing an inducible promoter, not only the nitrile hydratase, but also the amidase, can be overexpressed in active form. In the case of amidase, far higher activity levels can be achieved than in the case of corresponding fermentation of the Rhodococcus cells.

The microorganism is then suspended in the desired form in an aqueous medium, such as water or a buffer solution. Suitable buffer solutions are, for example, phosphate buffer, for instance K/Na phosphate buffer, PBS buffer, butyrate buffer, citrate solutions, etc. The pH of the buffer solution used should be in the range from pH 4.5 to pH 11, preferably from 5.5 to 8.5.

The resultant suspension is then admixed with the corresponding chiral cyanohydrin. Since the chiral cyanohydrins are lipophilic compounds of restricted water solubility, the use of a solubilizer as cosolvent is necessary to bring the cyanohydrins into solution in the aqueous medium.

Suitable solubilizers are, for example, organic solvents, surfactants, phase-transfer catalysts, etc.

Organic solvents which are suitable as cosolvent for the inventive method are those which firstly can dissolve the substrate sufficiently and secondly have as little as possible adverse effect on the enzyme activity.

Examples of these are dimethyl sulfoxide (DMSO), dimethylformamide (DMF), $C_1$-$C_6$-alcohols, for instance methanol, ethanol, isopropanol, 1-butanol, 2-butanol, tert-butanol or 1-pentanol, toluene or tert-butyl methyl ether (TBME) or mixtures thereof.

Preferably, as cosolvent, use is made of DMSO, DMF, ethanol, isopropanol or mixtures thereof, and particularly preferably DMSO and DMF.

The cosolvent fraction should be between 0.5 and 20% by volume, based on the total volume of the reaction solution.

Preferably, the cosolvent fraction is between 1 and 15% by volume, and particularly preferably between 2 and 10% by volume.

The substrate concentration in the reaction solution should be in the inventive method in the range from 1 g/l to 100 g/l (based on the total volume of the reaction solution), the acceptance of a sufficiently high substrate concentration being the fundamental precondition for use of the inventive enzymatic hydrolysis on a preparative scale.

Preference is given to substrate concentrations up to 50 g/l, particularly preferably up to 25 g/l.

The substrate concentration which is possible to react depends on the enzyme quantity used. For efficient quantitative reaction, the first hydrolysis step must proceed very rapidly in order to avoid decomposition of the cyanohydrin and the resultant racemization, so that relatively high cell densities are required.

It is necessary to note in this case that sufficient mixing of the reaction system is ensured.

The cell quantity or enzyme quantity depends on the activity of the microorganism in the form used, and also on the substrate concentration and the cosolvent.

The pH of the reaction mixture should be between 4.5 and 11, preferably between 5.5 and 8.

If appropriate, in addition a suitable acid or acid salt, for instance phosphoric acid, boric acid, citric acid, etc. can be added to the reaction mixture to set the pH.

The inventive enzymatic hydrolysis is carried out at a temperature of 10 to 60° C., preferably at 15 to 50° C., and particularly preferably at 20 to 45° C.

After hydrolysis has been carried out to give the desired chiral α-hydroxycarboxylic acids, they are isolated from the reaction mixture by means of a known technique, for instance centrifuging of the cells, extraction of the product after acidification by HCl (e.g.: pH 2) and if appropriate further purification by activated carbon filtration and recrystallization.

By means of the inventive use of Rhodococcus erythropolis NCIMB 11540, thus polar nitrites, such as chiral cyanohydrins, are converted in a simple and efficient manner under mild conditions into the conjugate chiral α-hydroxycarboxylic acids, with no racemization occurring. The desired α-hydroxycarboxylic acids are obtained, depending on the ee value of the cyanohydrin used, in a high optical purity of up to above 99% and at high yields of up to over 98%.

EXAMPLE 1

Production of the Biocatalyst

For the production of biomass of *Rhodococcus erythropolis* NCIMB 11540, a complex standard medium (medium A, see Table 1) was used. The strains were maintained on agar plates using medium A (solidification using 15 g/l of agar). The plates were sealed by lateral wrapping with parafilm and stored in a refrigerator at 4° C.

Growth of the liquid cultures was performed in 1000 ml conical flasks having chicanes using 250 ml of medium A at 30° C. and 130 rpm.

Variant I (without preculture): About half of the biomass of an agar plate was suspended in 5 ml of sterile physiological common salt solution. One cell suspension was added to 250 ml of culture medium.

Variant II (with preculture): For the preculture, some biomass of an agar plate was suspended in 5 ml of sterile physiological common salt solution. One cell suspension was added to 100 ml of culture medium (=preculture). After growth for 20-24 h, 5 ml of this preculture was added to 250 ml of culture medium.

The cells were harvested by centrifugation at approximately 3000 rpm for 30 min at 0-4° C. The cells were washed once with K/Na phosphate buffer (50 mM, pH 6.5). Then, the cells were resuspended in fresh buffer and either lyophilized after shock freezing (reactions with lyophilized cells, Example 2), or this cell suspension (approximately 6-8% of the culture volume) was used directly for the biocatalytic reactions (reactions with resting cells, Example 3).

TABLE I

Composition of medium A

| Sterilization group | Substance | Concentration [g/l] |
|---|---|---|
| I | $Na_2HPO_4$ | 4.97 |
|  | $KH_2PO_4$ | 2.04 |
| II | $MgSO_4 \cdot 7H_2O$ | 0.2 |
| III | $CaCl_2 \cdot 2H_2O$ | 0.02 |
|  | Ammonium iron(III) citrate | 0.05 |
|  | Trace solution SL-6 | 1 ml/l |
| IV | Yeast extract | 1 |
|  | Meat peptone | 10 |
| V | Glucose | 10 |

EXAMPLE 2

Reactions Using Lyophilized Cells on an Analytical Scale 31.6 mg, 52.6 mg and 105.2 mg of lyophilized cells were rehydrated in 10 ml of phosphate buffer (50 mM, pH 6.5) for approximately 1 hour at 130 rpm and 20-25° C. 475 µl aliquots of this cell suspension were transferred to 1.5 ml Eppendorf reaction vessels and admixed with 25 µl of an approximately 200 mM substrate solution of 2-hydroxy-4-phenylbutyronitrile in DMSO (3 mg, 5 mg and 10 mg of cells/ml, substrate concentration approximately 10 mM, 5% DMSO). The reaction was carried out in the Thermomixer at 30° C. and 1000 rpm. After 0, 2, 4, 6, 8, 10, 15, 20, 30, 60 and 120 minutes, in each case one Eppendorf reaction vessel was admixed with 0.5 ml of 1N HCl. After centrifugation (5 min, 13 000 rpm) and corresponding dilution, the concentrations of cyanohydrin, hydroxyamide and hydroxy acid were determined by HPLC.

TABLE 2

Hydrolysis of 2-hydroxy-4-phenylbutyronitrile by lyophilized *Rhodococcus erythropolis* NCIMB 11540 cells (10 mg of cells/ml; substrate concentration: 10 mM) concentration (mM) of substrate, hydroxyamide and hydroxycarboxylic acid as a function of time (min)

|  | 0 min | 10 min | 20 min | 30 min | 60 min | 100 min | 120 min |
|---|---|---|---|---|---|---|---|
| Substrate | 10 mM | 1.9 mM | 0.7 mM | 0.25 mM | 0 mM | 0 mM | 0 mM |
| Amide | 0 mM | 4.7 mM | 3.5 mM | 3.2 mM | 2 mM | 1.1 mM | 0.5 mM |
| Acid | 0 mM | 3.3 mM | 5.4 mM | 6.1 mM | 7.5 mM | 8.2 mM | 8.5 mM |

EXAMPLE 3

Enzymatic Hydrolysis Using Resting Cells and Lyophilized Cells

The biocatalyst was produced in a similar manner to Example 1, Variant I, 2 culture flasks. After 20 hours ($OD_{546}$=3.5 and 1.8), cells were centrifuged off from 4 times 10 ml aliquots of fermentation broth and washed once with K/Na—$PO_4$ buffer (pH 6.5, 50 mM). Two of the cell samples were lyophilized before activity determination, and the other two were used as resting cells.

The cells were resuspended in 1.8 ml K/Na—$PO_4$ buffer (pH 6.5, 50 mM) (lyophilized cells were shaken for 1 h for rehydration). The reaction was started by adding 200 µl of a 200 mM substrate solution in DMSO (substrate concentration approximately 20 mM) and carried out at 30° C. and 130 rpm in the shaking cabinet. After 30 min, 60 min and 17 h, 200 µl were withdrawn and admixed with 200 µl of 1N HCl. After centrifugation (5 min, 13 000 rpm) and dilution, the conversion rates were determined by means of HPLC. Only the substrate and the two products were taken into consideration in this. The substrate used was (R)-2-chloromandelonitrile (ee>99%). The results are shown in Tab. 3.

TABLE 3

Results of the reactions of culture 1 ($OD_{546}$ 3.5), substrate: (R)-2-chloromandelonitrile

|  | Resting cells | | Lyophilized cells (19 mg/ml) | |
|---|---|---|---|---|
|  | Conversion rate CH [%][1] | Conversion rate HA [%][2] | Conversion rate CH [%][1] | Conversion rate HA [%][2] |
| 30 min | 100 | 2 | 40 | <1 |
| 60 min | — | 4 | 41 | 0 |
| 17 h | — | 42 | 43 | <1 |

[1]The conversion rate of cyanohydrin (CH) relates to both products (hydroxyamide and hydroxy acid).
[2]The conversion rate of hydroxyamide (HA) is based on the amount of hydroxy acid which was formed from the hydroxyamide present.

EXAMPLE 4

Enzymatic Hydrolysis Using Different Substrate Concentrations

Experiment 4.1:

In experiment 4.1, the reaction was carried out on an analytical scale (reaction volume 1 ml) using 3 substrate concentrations (2.2 g/l, 6.6 g/l, 13.2 g/l).

The biocatalyst was produced according to Example 1, Variant II, 2 l of fermentation medium, harvest after 20 hours ($OD_{546}$ 6.1). The cells from 8 times 10 ml of fermentation solution were centrifuged off in culture tubes. The resultant cell mass was washed once in each case with 2 ml K/Na-phosphate buffer (pH 6.5, 50 mM). The contents of 2 tubes were lyophilized for determining the dry weight.
Weight: 1. 37 mg of lyophilized cells/10 ml fermentation solution
2. 30 mg
(This amount corresponded to approximately the use of cells/ml in the following reactions.)

The contents of the remaining 6 tubes were resuspended in 950 µl of buffer (OD approximately 40) and transferred to Eppendorfs. To each of these cell suspensions were added 50 µl of variously concentrated substrate solutions (3 concentrations, parallel batches, 5% DMSO as cosolvent). The Eppendorfs were shaken on the Thermomixer at 30° C. and 1000 rpm. For monitoring the conversion rate, in each case 200 µl were withdrawn and admixed with 200 µl of 1N HCl. After centrifugation (5 min, 13 000 rpm) and dilution, the conversion rates were determined by HPLC.

Following concentrations of (R)-2-chloromandelonitrile were used:
a. Substrate solution: 11 mg of (R)-2-chloromandelonitrile in 250 µl of DMSO (approximately 260 mM)
  Substrate concentration in the batch: 2.2 g/l (13.1 mM)
b. Substrate solution: 33 mg of (R)-2-chloromandelonitrile in 250 µl of DMSO (approximately 290 mM)
  Substrate concentration in the batch: substrate concentration: 6.6 g/l (39.4 mM)
c. Substrate solution: 66 mg of (R)-2-chloromandelonitrile in 250 µl of DMSO (approximately 1580 mM)
  Substrate concentration in the batch: 13.2 g/l (78.8 mM)

The batches a-c are compared in Table 4.1 with reference to the formation of 2-chloromandelic acid (in %). In all batches, the hydroxy acid was formed quantitatively. It was found that even relatively high substrate concentrations are accepted without problems.

TABLE 4.1

Comparison of batches a-c with reference to the formation of (R)-2-chloromandelic acid in %

|   | 10 min | 20 min | 30 min | 40 min | 50 min |
|---|--------|--------|--------|--------|--------|
| a | 77%    | 86%    | 92%    | 94%    | 96%    |
| b | 45%    | 70%    | 82%    | 89%    | 95%    |
| c | 58%    | 85%    | 96%    | 98%    | 100%   |

Experiment 4.2:

In experiment 4.2, the reaction was carried out using 2 different substrate concentrations (10 g/l, 20 g/l) on a 5 ml scale.

The biocatalyst was produced according to Example 1, Variant II, 2 l fermentation medium, harvest after 19 hours ($OD_{546}$ 8.4). The cells were resuspended in approximately 140 ml of buffer (resting cells, $OD_{546}$ 52). In each case 4.75 ml of this cell suspension were used for the enzymatic reactions.

Two different concentrations of (R)-2-chloromandelonitrile were studied in parallel batches. The reaction was started by adding 250 µl of substrate solution and was carried out in culture tubes in the shaking cabinet at 30° C. and 130 rpm. To monitor the conversion rate, in each case 200 µl were withdrawn and admixed with 200 µl of 1N HCl. After centrifugation (5 min, 13 000 rpm) and dilution, the conversion rates were determined by HPLC.
a. 50 mg of (R)-2-chloromandelonitrile, dissolved in 250 µl of DMSO ([S]=60 mM, 10 g/l, cosolvent: 5% DMSO)
  As soon as after 30 minutes, all of the cyanohydrin had reacted to form the hydroxyamide, after 2 h, approximately 40% of hydroxy acid were formed. After 20 h, the reaction was quantitative.
b. 100 mg of (R)-2-chloromandelonitrile, dissolved in 250 µl of DMSO ([S]=120 mM, 20 g/l, cosolvent: 5% DMSO)
  As soon as after 30 minutes, all of the cyanohydrin had reacted to form the amide, after 18 h, 36% of hydroxy acid were formed. After 43 h, 41% of hydroxy acid were formed, thereafter no further reaction took place.

Experiment 4.3:

In experiment 4.3, reactions were carried out using 10 g/l and 15 g/l of (R)-2-chloromandelonitrile. In addition, after complete conversion, the ee of the hydroxy acid formed was determined.

The biocatalyst was produced according to Example 1, Variant II, 2.75 l of the fermentation medium, harvest after 20 hours. The cells were resuspended in approximately 200 ml of buffer (resting cells, $OD_{546}$ 44). In each case 4.85 ml of this cell suspension were used for the enzymatic reactions.

Two different concentrations of (R)-2-chloromandelonitrile were studied in parallel batches. The reaction was started by adding 150 µl of substrate solution and was carried out in culture tubes in the shaking cabinet at 40° C. and 150 rpm. The conversion rate was monitored by means of HPLC. At complete conversion, the hydroxy acid was extracted after acidification and the ee was determined.
a. 50 mg of (R)-2-chloromandelonitrile, dissolved in 150 µl of DMSO ([S]=60 mM, 10 g/l, cosolvent: 3% DMSO)
  As soon as after 30 minutes, all of the cyanohydrin had reacted to form the amide, after 2 h 80% of hydroxy acid were formed, after 19 h the hydrolysis to form the hydroxy acid was complete (product ee>99%).
b. 75 mg of (R)-2-chloromandelonitrile, dissolved in 150 µl of DMSO ([S]=90 mM, 15 g/l, cosolvent: 3% DMSO)
  As soon as after 30 minutes, all of the cyanohydrin had reacted to form the amide, after 2 h, approximately 60% of hydroxy acid were formed, after 19 h the hydrolysis to form the hydroxy acid was complete (product ee=99%).

EXAMPLE 5

Enzymatic Hydrolysis Using Different Cosolvents

Experiment 5.1:

In reactions on a 50 ml scale, DMSO was compared with EtOH as cosolvent. 5% cosolvent were used, but the substrate concentration was only 4 g/l (R)-2-chloromandelonitrile.

Biomass from 8 times 250 ml (minus 80 ml, see Experiment 4.1) of fermentation medium (OD approximately 6.1) was harvested after 20 h. The cells were suspended in 100 ml of K/Na-phosphate buffer (pH 6.5, 50 mM). This cell suspension (OD 60) was used for the enzymatic reactions. The reactions of (R)-2-chloromandelonitrile, dissolved in DMSO or EtOH were carried out in 100 ml ground glass joint conical flasks at 150 rpm and 30° C. To monitor the conversion rate by means of HPLC, in each case 200 µl of sample were admixed with 200 µl of 1N HCl, centrifuged (5 min, 13 000 rpm) and diluted before measurement. After complete conversion, the ee of the product was determined.

a. 50 ml of cell suspension were admixed with 200 mg of (R)-2-chloromandelonitrile (>99%) dissolved in 2300 µl of DMSO and 200 µl of 0.1% $H_3PO_4$.

Substrate concentration: 4 g/l (24 mM), 5% DMSO as cosolvent

Product ee of (R)-2-chloromandelic acid: 97% b. 50 ml of cell suspension are admixed with 200 mg of (R)-2-chloromandelonitrile (>99%) dissolved in 2300 µl of EtOH and 200 µl of 0.1% $H_3PO_4$.

Substrate concentration: 4 g/l (24 mM), 5% EtOH as cosolvent

Product ee of (R)-2-chloromandelic acid: >99%

Experiment 5.2:

Here, the solvents DMSO, EtOH and $^i$PrOH were again used at a fraction of 5%; the substrate concentration was 10 g/l of (R)-2-chloromandelonitrile. The reaction was carried out on a 5 ml scale.

Production of the biocatalyst Example 4, Experiment 4.2 ($OD_{546}$ 8.4). In each case 4.75 ml of the cell suspension (resting cells, $OD_{546}$ 52) were used for the enzymatic reactions. Reactions of (R)-2-chloromandelonitrile (>99%) dissolved in DMSO, EtOH and i-PrOH were carried out in culture tubes at 150 rpm and 30° C. (parallel batches).

To monitor the conversion rate by means of HPLC, in each case 200 µl of sample were admixed with 200 µl of 1N HCl, centrifuged (5 min, 13 000 rpm) and diluted before measurement. After complete conversion, the ee of the product was determined.

a. 50 mg of (R)-2-chloromandelonitrile, dissolved in 250 µl of DMSO ([S]=60 mM, 10 g/l, cosolvent: 5% DMSO)

As soon as after 30 minutes, all of the cyanohydrin had reacted to form the hydroxyamide, after 2 h, approximately 40% of hydroxy acid were formed. After 20 h the reaction was quantitative (product ee=95%).

b. 50 mg of (R)-2-chloromandelonitrile, dissolved in 250 µl of EtOH ([S]=60 mM, 10 g/l, cosolvent: 5% EtOH)

As soon as after 30 minutes, all of the cyanohydrin had reacted to form the amide, after 3 h, 35% of hydroxy acid were formed. After 19 h, the hydrolysis to form the hydroxy acid was 94% complete, and after 28 h, the reaction is virtually complete (product ee=97%).

c. 50 mg of (R)-2-chloromandelonitrile, dissolved in 250 µl of i-PrOH, ([S]=60 mM, 10 g/l, cosolvent: 5% i-PrOH)

As soon as after 30 minutes, all of the cyanohydrin had reacted to form the amide, after 3 h, 8% of hydroxy acid were formed. After 44 h, 64% of hydroxy acid were formed (product ee=92.3).

EXAMPLE 6

Enzymatic Hydrolysis at Different Temperatures

Experiment 6.1:

In Experiment 6.1, the course of the reaction was compared at reaction temperatures of 30° C., 35° C. and 40° C. The batches were carried out on a 5 ml scale using a substrate concentration of 10 g/l of (R)-2-chloromandelonitrile. After complete reaction, the ee of the product was determined.

The biocatalyst was produced according to Example 4, Experiment 4.2 ($OD_{546}$ 8.4). In each case 4.75 ml of the cell suspension (resting cells, $OD_{546}$ 52) were used for the enzymatic reactions. Reactions of 50 mg of (R)-2-chloromandelonitrile (>99%) ([S]=60 mM, 10 g/l), dissolved in 250 µl of DMSO (5%) were carried out at 3 different temperatures (30° C., 35° C., 40° C.) in culture tubes at 150 rpm (parallel batches).

To monitor the conversion rate by means of HPLC, in each case 200 µl of sample were admixed with 200 µl of 1N HCl, centrifuged (5 min, 13 000 rpm) and diluted before measurement. After complete reaction, the ee of the product was determined.

a. T=30° C.

As soon as after 30 minutes, all of the cyanohydrin had reacted to form the amide, after 2 h, 42% of hydroxy acid were formed, after approximately 20 h the hydrolysis to form (R)-2-chloromandelic acid was complete (product ee=95%).

b. T=35° C.

As soon as after 30 minutes, all of the cyanohydrin had reacted to form the amide, after 2 h, 65% of hydroxy acid were formed, after 19 h the hydrolysis to form (R)-2-chloromandelic acid was complete (product ee=96.5%).

c. T=40° C.

As soon as after 30 minutes, all of the cyanohydrin had reacted to form the amide, after 2 h, 86% of hydroxy acid were formed, after 19 h, the hydrolysis to form (R)-2-chloromandelic acid was complete (product ee=97.9%).

Experiment 6.2:

In Experiment 6.2, the temperature was increased to 50° C.

The biocatalyst was produced according to Example 4, Experiment 4.3 ($OD_{546}$ 44). In each case 4.85 ml of the cell suspension (resting cells, $OD_{546}$ 44) were used for the enzymatic reactions. Reactions of 50 mg of (R)-2-chloromandelonitrile (>99%) ([S]=60 mM, 10 g/l), dissolved in 150 µl DMSO (3%) were carried out at 3 different temperatures (30° C., 40° C., 50° C.) in culture tubes at 150 rpm (parallel batches).

To monitor the conversion rate by means of HPLC, in each case 200 µl of sample were admixed with 200 µl of 1N HCl, centrifuged (5 min, 13 000 rpm) and diluted before measurement. After complete reaction, the ee of the product was determined.

a. T=30° C.

As soon as after 30 minutes, all of the cyanohydrin had reacted to form the amide, after 2 h, 42% of hydroxy acid were formed, after 19 h, the hydrolysis to form the hydroxy acid was complete (product ee>99%).

b. T=40° C.

As soon as after 30 minutes, all of the cyanohydrin had reacted to form the amide, after 2 h, 80% of hydroxy acid were formed, after 19 h the hydrolysis to form hydroxy acid was complete (product ee>99%).

c. T=50° C.

As soon as after 30 minutes, all of the cyanohydrin had reacted to form the amide, after 2 h, 92% of hydroxy acid were formed, after 19 h, the hydrolysis to form hydroxy acid was complete (product ee>99%).

EXAMPLE 7

Reactions of Cyanohydrins of Aldehydes in the Presence of *Rhodococcus erythropolis* NCIMB 11540 on a Semipreparative Scale For all reactions, K/Na-phosphate buffer (50 mM, pH 6.5) was used. The reaction was followed by HPLC. After sampling, to stop the biocatalytic reaction, sample volumes were admixed with 1N HCl (parallel samples). After centrifugation (5 min, 13 000 rpm), the samples were diluted with HPLC eluent.

For workup, the biomass was centrifuged off for 30 min at 4° C. and 3000 rpm and washed once with distilled $H_2O$. After acidifying the supernatant with 1N HCl to pH 2, it was extracted 3-4 times with TBME.

Experiment 7.1:

The biocatalyst was produced according to Example 1, Variant II. 3 l fermentation medium, harvest after 20 hours ($OD_{546}$ 5.9). The cells were resuspended in buffer to make approximately 180 ml (resting cells, $OD_{546}$ 80). 0.6 g (R)-2-chloromandelonitrile (ee>99%), dissolved in 1.5 ml of DMSO was admixed with 60 ml of this cell suspension. The hydrolysis was carried out at 30° C. and 150 rpm in the shaking cabinet. After 30 min, the cyanohydrin was completely hydrolyzed, after 17 hours, the reaction to give (R)-2-chloromandelic acid was complete.

Crude yield: 0.73 g (109%)
Product ee: >99%

Experiment 7.2:

In Experiment 7.2, some reaction parameters were varied. Standard conditions were 10 g/l of substrate and DMSO as cosolvent (here 2.5%). A second batch was carried out using 15 g/l of substrate, a further with 10 g/l of substrate and DMF as cosolvent.

The biocatalyst was produced according to Example 1, Variant II. 3 l of fermentation medium, harvest after 20 hours ($OD_{546}$ 6.8). The cells were resuspended to give approximately 190 ml of buffer (resting cells, $OD_{546}$ 69). Three reactions were carried out.

Batch A: 0.3 g of (R)-2-chloromandelonitrile (ee>99%), dissolved in 750 µl of DMSO were admixed with 30 ml of this cell suspension. The hydrolysis was carried out at 40° C. and 150 rpm in the shaking cabinet. After 30 min, the cyanohydrin was completely hydrolyzed, after 5 hours the reaction to give (R)-2-chloromandelic acid was complete.

Crude yield: 0.31 g (93%)
Product ee: >99%

Batch B: 0.3 g of (R)-2-chloromandelonitrile (ee>99%), dissolved in 750 µl of DMF were admixed with 30 ml of this cell suspension. The hydrolysis was carried out at 40° C. and 150 rpm in the shaking cabinet. After 30 min, the cyanohydrin was completely hydrolyzed, after 5 hours the reaction to give (R)-2-chloromandelic acid was complete.

Crude yield: 0.30 g (90%)
Product ee: 98.5%

Batch C: 0.45 g of (R)-2-chloromandelonitrile (ee>99%), dissolved in 750 µl of DMSO, were admixed with 30 ml of this cell suspension. The hydrolysis was carried out at 40° C. and 150 rpm in the shaking cabinet. After 30 min, the cyanohydrin was completely hydrolyzed, after 5 hours the reaction to give (R)-2-chloromandelic acid was virtually complete.

Crude yield: 0.45 g (90%)
Product ee: >99%

Experiment 7.3:

Here, 2 batches having differing substrate concentration (batch A 10 g/l, batch B 15 g/l) were carried out. Both reactions proceeded virtually at the identical speed and were complete after 2 hours.

The biocatalyst was produced according to Example 1, Variant II. 3 l fermentation medium, harvest after 20 hours ($OD_{546}$ 1.2). The cells were resuspended in approximately 180 ml of buffer (resting cells, $OD_{546}$ 70). Two reactions were carried out.

Batch A: 0.8 g (R)-2-chloromandelonitrile (ee>99%), dissolved in 1.6 ml of DMSO, were added to the cell suspension (80 ml). The hydrolysis was carried out at 50° C. and 150 rpm in the shaking cabinet. After 15 min, the cyanohydrin was completely hydrolyzed, after 2 hours, the reaction to give (R)-2-chloromandelic acid was complete.

Crude yield: 0.85 g (95%)
Product ee: >99%

Batch B: 1.2 g (R)-2-chloromandelonitrile (ee>99%), dissolved in 1.6 ml of DMSO, were added to the cell suspension (80 ml). The hydrolysis was carried out at 50° C. and 150 rpm in the shaking cabinet. After 30 min, the cyanohydrin was completely hydrolyzed, after 2 hours, the reaction to give (R)-2-chloromandelic acid was complete.

Crude yield: 1.26 g (94%)
Product ee: 98.9%

Experiment 7.4:

The biocatalyst was produced according to Example 1, Variant II. 2.5 l of fermentation medium, harvest after 20 hours ($OD_{546}$ 6.9). The cells were resuspended in approximately 160 ml of buffer (resting cells, $OD_{546}$ 63).

1.3 g of (R)-2-chloromandelonitrile (ee>99%), dissolved in 2.5 ml of DMSO, were added to 140 ml of this cell suspension. The hydrolysis was carried out at 40° C. and 150 rpm in the shaking cabinet. After 15 min, the cyanohydrin was completely hydrolyzed, after 3 hours the reaction to give (R)-2-chloromandelic acid was complete.

Crude yield: 1.43 g (98%)
Product ee: >99%

Experiment 7.5:

In this reaction, 1 g of mandelonitrile was hydrolyzed at a substrate concentration of 8 g/l to give the corresponding hydroxy acid.

The biocatalyst was produced according to Example 1, Variant II. 2 l of fermentation medium, harvest after 20 hours ($OD_{546}$ 8.4). The cells were resuspended in approximately 120 ml of buffer (resting cells, $OD_{546}$ 74). The reaction, after deep-freezing of the biocatalyst, was carried out overnight.

1.0 g of (R)-(+)-mandelonitrile, dissolved in 2.4 ml of DMSO, was added to the cell suspension (120 ml). The hydrolysis was carried out at 40° C. and 150 rpm in the shaking cabinet. After 15 min, the cyanohydrin was completely hydrolyzed, after 5 hours the reaction to give (R)-mandelic acid was complete.

Crude yield: 1.16 g (100%)
Product ee: 93%

EXAMPLE 8

Reactions of Cyanohydrins of Ketones in the Presence of *Rhodococcus erythropolis* NCIMB 11540 on a Semipreparative Scale A K/Na phosphate buffer (50 mM, pH 6.5) was used. The reaction was followed by TLC.

For the workup, the biomass was centrifuged off for 20 min at 4° C. and 6000 rpm and washed once with distilled $H_2O$. After acidifying the supernatant with 1N HCl to pH 2, it was extracted 3-4 times with TBME.

The biocatalyst was produced according to Example 1, Variant II. 2 l of fermentation medium, harvest after 20 hours. The cells were resuspended in approximately 60 ml of buffer (resting cells, $OD_{546}$ 60).

300 mg of (S)-acetophenone cyanohydrin (25% acetophenone, ee 94%), dissolved in 1 ml of DMSO, were added to the cell suspension. After 20 h, the reaction was complete according to TLC and the product (containing 1-phenylethanol and traces of other impurities) was extracted. The reaction proceeded without loss of enantiomeric purity.

Crude yield: 357 mg

EXAMPLE 9

Generation of Enzyme Preparations of Nitrile Hydratase and Amidase for Hydrolysis of Substituted Cyanohydrins by Means of Recombinant Expression in *E. coli*

For expression of the nitrile hydratase, and also for the expression of the amidase, the pMS470 plasmid system was used. In addition to the replicated elements, this plasmid has a selectable ampicillin resistance and the Lac repressor gene lacI via an inducible tac promoter, which permits controlled overexpression of the cloned open reading frame.

Expression Plasmid for the *Rhodococcus erythropolis* NCIMB 11540 Nitrile Hydratase:

The plasmid map may be seen in FIG. 1. The plasmid bears the name pMS470Nhse7.3. In addition to the two gene sections of the nitrile hydratase (α- and β-subunit) it also contains a third open reading frame which codes for an activator protein.

Expression Plasmid for the *Rhodococcus erythropolis* NCIMB 11540 Amidase:

Other than the case with nitrile hydratase, for the expression of the amidase of *Rhodococcus erythropolis* NCIMB 11540 only a single reading frame is necessary, and this was cloned in plasmid pMS470-33/3/1/11 downstream of the tac promoter. FIG. 2 shows the plasmid map of this construct.

Fermentation of the Recombinant Nitrite Hydratase and Amidase

Fermentation of the two enzymes was always performed by the general protocol developed for overexpression of enzymes in the pMS470 system.

Here, samples were:
  inoculated from an overnight culture (ONC) into a main culture containing LB medium and antibiotic, in the shaking flask.
  allowed to grow to the exponential phase
  at $OD_{600}$ (optical density at 600 nm) 0.8 to 1.5, induced with IPTG (isopropylthiogalactopyranoside)
  further induced for 18 h (protein expression)
  harvested (centrifugation) and disintegrated (ultrasound)

Expression of the Nitrile Hydratase

The *E. coli* B BL21 cells transformed by pMS470Nhase7.3 (or pMSNhasetactac7.3) were isolated on LB-ampicillin plates and an ONC of 100 ml of LB-ampicillin medium was inoculated with an individual colony. On the next morning a main culture consisting of 250 ml of LB-ampicillin medium was inoculated in a 1000 ml chicane flask to an $OD_{600}$ of 0.01 to 0.03 (Beckmann Photometer). The growth temperature was controlled at 25° C., since at higher temperatures insoluble inclusion bodies are formed exclusively. After the induction density was reached ($OD_{600}$=1 Beckmann Photometer), the cultures were induced by adding IPTG to give a concentration of 0.1 mM. In addition, the media were supplemented with 0.1 mM ammonium iron(III) citrate. After reaching an $OD_{600}$>4, the cultures were harvested (centrifugation at approximately 3000·g for 15 min) and washed once with approximately 100 ml of PBS buffer. The cell pellet was then resuspended in PBS buffer (approximately 5 ml total volume) and disintegrated using a ultrasonic probe (BRANSON Sonifier 250, 60% power setting, constant sonication; 5 times 30 s each time with a 1 min pause for cooling) (visual control of completeness under the microscope). The resultant crude lysates had a typical activity of approximately 100-250 U/ml (approximately 350-500 U/ml for pMSNhasetactac7.3), analyzed using methacrylonitrile as substrate under the conditions listed hereinafter.

For preservation, the lysates were stored at −20° C. Storage at room temperature is associated with rapid loss of activity.

Activity determination: crude lysates were diluted 1:10 with PBS buffer immediately before activity determination. 1.4 ml of a 40 mM methacrylonitrile solution in PBS buffer were admixed with 20 µl of the diluted lysate and incubated at 28° C. (Eppendorf Thermomixer 5436). At the time point 0, 1, 2, 5, 10 and 15 minutes, 200 µl samples were withdrawn and immediately the enzyme reaction was stopped in these samples by 800 µl of 0.17% phosphoric acid. After centrifugation (16 000·g, 10 minutes), the samples were analyzed spectrophotometrically at 224 nm (Perkin Elmer UV/VIS Spectrometer Lambda Bio). The increase in extinction was correlated with the increase in concentration of methacrylamide, an $\epsilon$ value of 0.57 $l \cdot mmol^{-1} \cdot cm^{-1}$ being used as a reference.

Expression of Amidase

The *E. coli* B BL21 cells transformed by pMS470-33/3/1/11 were isolated on LB-ampicillin plates and an ONC of 100 ml of LB-ampicillin medium was inoculated with an individual colony. On the next morning a main culture consisting of 250 ml of SOC-ampicillin medium was inoculated into a 1000 ml chicane flask to an $OD_{600}$ of 0.01 to 0.03 (Beckmann Photometer). The growth temperature was controlled to 30° C., since fermentation at 37° C. leads exclusively to the formation of insoluble and inactive protein. After reaching the induction density ($OD_{600}$=1 Beckmann Photometer), the cultures were induced by adding IPTG to a concentration of 0.3 mM. After an induction time of 16 h, the cells were harvested (centrifugation 3000·g, 10 min) and washed with sodium phosphate buffer (0.1 M, pH=7). The pellet produced was resuspended to approximately 5 ml total volume in wash buffer and disintegrated using an ultrasound probe (BRANSON Sonifier 250, 60% power setting, constant sonication; 5 times 30 s each with 1 min pause for cooling) with constant cooling to completeness (visual control of completeness under the microscope). The crude lysates thus produced were frozen for preservation at −20° C. The lysates had an activity of approximately 75 U/ml, determined using acetamide (40 mM) as substrate in PBS buffer at 37° C. (determination of released ammonium by the indophenolblue method).

Determination of Amidase Activity:

The following solutions were used:
Substrate solution: 40 mM acetamide in PBS
Solution A: 10% (w/v) phenol in ethanol (95%)
Solution B: 0.5% (w/v) nitroprusside sodium in $ddH_2O$
Solution C: 100 g of trisodium citrate and 5 g of sodium hydroxide in 550 ml of water
Solution D: 600 ml of commercially conventional sodium hypochlorite solution diluted to 1000 ml
Ammonium standards: 0, 80, 120, 200, 280, 400 µg/l of ammonium sulfate in water 1.4 ml of substrate solution were incubated at 30° C. (Eppendorf Thermomixer 5436) with 10 µl of enzyme dilution (1:10 in PBS). The enzyme reaction was stopped in 100 µl samples after 0, 1, 2, 5, 10 and 15 minutes using 20 µl of solution A. After withdrawal of the last sample, the resultant solutions were diluted with 400 µl of water. For calibration, in addition, ammonium standard solutions (each 500 ml) were admixed with 20 µl of solution A. To samples and also to standards, thereupon 20 µl of solution B and 50 µl of a mixture of 4 parts of solution C with 1 part of solution D were added by pipette. Good mixing was ensured by vortexing. The resultant samples and standards were stood at 37° C. for 15 min. The resultant blue coloration, after dilution of all samples and standards 1:10) with water, was quantified in the spectrophotometer (Perkin Elmer UV/VIS Spectrometer Lambda Bio) at 640 nm. By correlating the increase in blue coloration over time with the extinction values of the standards, the activity (µmol of released ammonium per minute) could be back-calculated.

EXAMPLE 10

Hydrolysis Using the Recombinant Enzyme

In these reactions, cloned nitrile hydratase of *Rhodococcus erythropolis* NCIMB 11540 was used as crude lysate of *E. coli* clone 7.3 (produced according to Example 9).

Procedure:

50 µl of crude lysate were diluted with 425 µl of buffer (K/Na—PO₄ buffer, pH 7, 50 mM) and admixed with 25 µl of an approximately 220 mM substrate solution in DMSO (5 mg of protein/ml substrate concentration approximately 10 mM, 5% DMSO). The reaction was carried out in the Thermomixer at 30° C. and 1000 rpm. After 0, 2, 4, 6, 8, 10, 15, 20, 30, 60 and 120 minutes, in each case one Eppendorf was admixed with 0.5 ml of 1N HCl. After centrifugation (5 min, 13 000 rpm) and corresponding dilution, the concentrations of cyanohydrin and hydroxyamide were determined by HPLC. The activity of the nitrile hydratase was determined from the velocity of formation of hydroxyamide (gradient in the initial range). The standard substrate (100% activity) used was 2-hydroxy-4-phenylbutyronitile. The activity in the hydrolysis of the other substrates was compared with the activity on 2-hydroxy-4-phenylbutyronitrile (Tab. 5).

Results:

The activity of the nitrile hydratase in the crude lysate of the *E. coli* clone 7.3 in the hydrolysis of 2-hydroxy-4-phenyl-butyronitrile was approximately 0.3 µmol·mg⁻¹·min⁻¹. In Table 5, activity on the different substrates is compared.

TABLE 5

Comparison of the activity of nitrile hydratase from *E. coli* clone 7.3 on the different substrates.

| Substrate | Activity of the nitrile hydratase [%] |
|---|---|
| OH<br>⌬—CH(CN)—CH₂—CH₂—Ph | 100 |
| OH<br>⌬—CH(CN)—(2-Cl-C₆H₄) | 100 |

TABLE 5-continued

Comparison of the activity of nitrile hydratase from *E. coli* clone 7.3 on the different substrates.

| Substrate | Activity of the nitrile hydratase [%] |
|---|---|
| OH<br>⌬—CH(CN)—(4-Me-C₆H₄) | 60 |

Reaction of (R)-2-chloromandelonitrile on a Semipreparative Scale 50 ml of a crude lysate of the cloned nitrile hydratase from *Rhodococcus erythropolis* NCIMB 11540 (*E. coli* clone 7.3, produced according to Example 9) were diluted with 100 ml of buffer (K/Na—PO₄ buffer, 50 mM, pH 6.5). After adding 1.0 g of (R)-2-chloromandelonitrile (ee>99%) in 1.5 ml of DMSO, the suspension was shaken at 150 rpm and 30° C. After complete reaction, the cell debris was centrifuged off and the product extracted continuously for 4 days with CH₂Cl₂.

ee of the crude product: >99%
Yield after purification: 0.91 g (82%)

The invention claimed is:

1. A method for producing chiral α-hydroxycarboxylic acids, which comprises converting (R)- or (S)-cyanohydrins by enzymatic hydrolysis in the presence of *Rhodococcus erythropolis* NCIMB 11540 into the conjugate (R)- or (S)-α-hydroxycarboxylic acids.

2. The method as claimed in claim 1, characterized in that (R)- or (S)-cyanohydrins are used as starting materials which are obtained by enzymatic or chemically catalyzed addition of a cyanide group to the corresponding aliphatic, aromatic or heteroaromatic aldehydes or ketones.

3. The method as claimed in claim 1, characterized in that (R)- or (S)-cyanohydrins of the formula

(I)

where R1 and R2 independently of one another are H, a C₁-C₆-alkyl or C₁-C₆-alkenyl radical which is optionally monosubstituted or polysubstituted by substituents inert under the reaction conditions, or a phenyl radical which is optionally monosubstituted or polysubstituted by substituents inert under the reaction conditions, with the proviso that R1 and R2 are not both H, are used.

4. The method as claimed in claim 1, characterized in that use is made of the microorganism *Rhodococcus erythropolis* NCIMB 11540 in the form of ground cells, immobilized cells, lyophilized cells, or "resting cells".

5. The method as claimed in claim 1, characterized in that the microorganism *Rhodococcus erythropolis* NCIMB 11540 is suspended in an aqueous medium and the resultant suspension is admixed with the corresponding chiral cyanohydrin in the presence of a solubilizer as cosolvent.

6. The method as claimed in claim 5, characterized in that, as solubilizer, use is made of organic solvents, surfactants, or phase-transfer catalysts.

7. The method as claimed in claim 6, characterized in that, as organic solvent, use is made of DMSO, DMF, $C_1$-$C_6$-alcohols, TMBE or mixtures thereof.

8. The method as claimed in claim 5, characterized in that the cosolvent fraction is between 0.5 and 20% by volume, based on the total volume of the reaction solution.

9. The method as claimed in claim 1, characterized in that the pH of the reaction mixture is between 4.5 and 11.

10. The method as claimed in claim 1, characterized in that the hydrolysis is carried out at a temperature between 10 and 60° C.

* * * * *